US011933699B2

(12) United States Patent
Chen et al.

(10) Patent No.: US 11,933,699 B2
(45) Date of Patent: Mar. 19, 2024

(54) DEVICES AND METHODS FOR PREPARING FILTERED SOLUTIONS FOR LATERAL FLOW TESTING

(71) Applicant: Waters Technologies Corporation, Milford, MA (US)

(72) Inventors: Lingyun Chen, Scarborough, ME (US); Chris Borbone, Sturbridge, MA (US)

(73) Assignee: Waters Technologies Corporation, Milford, MA (US)

( * ) Notice: Subject to any disclaimer, the term of this patent is extended or adjusted under 35 U.S.C. 154(b) by 732 days.

(21) Appl. No.: 16/021,882

(22) Filed: Jun. 28, 2018

(65) Prior Publication Data

US 2019/0011333 A1    Jan. 10, 2019

Related U.S. Application Data

(60) Provisional application No. 62/529,230, filed on Jul. 6, 2017.

(51) Int. Cl.
*G01N 1/14* (2006.01)
*E02F 3/90* (2006.01)
(Continued)

(52) U.S. Cl.
CPC ............... *G01N 1/14* (2013.01); *G01N 1/34* (2013.01); *G01N 1/4077* (2013.01); *G01N 11/08* (2013.01);
(Continued)

(58) Field of Classification Search
CPC ........... G01N 1/4005; B01L 2300/0681; B01L 2300/0825
See application file for complete search history.

(56) References Cited

U.S. PATENT DOCUMENTS

2003/0064526 A1* 4/2003 Niedbala ............... B01L 3/5029
436/165
2009/0269859 A1* 10/2009 Liu ..................... B01D 15/3809
436/541
(Continued)

FOREIGN PATENT DOCUMENTS

EP           2676606 A1   12/2013
WO       2016/149235 A1    9/2016
WO    WO-2016149235 A1 *  9/2016  ............... C12M 1/34

OTHER PUBLICATIONS

Meng et al. "Recent advances in membrane bioreactors (MBRs): Membrane fouling and membrane material" (Water Research, 2009, 43, p. 1489-1512) (Year: 2009).*

(Continued)

*Primary Examiner* — Ryan B Huang
(74) *Attorney, Agent, or Firm* — WOMBLE BOND DICKINSON (US) LLP; Deborah M. Vernon; Mark R. Deluca

(57) ABSTRACT

The present disclosure relates to devices and methods for preparing a filtered solution from slurry for lateral flow testing of analytes of interest in agricultural or environmental samples. A porous frit is located adjacent to an outlet of a vessel containing slurry, and positive pressure is applied to the volume enclosed by a vessel body of the vessel to cause the slurry to pass through the porous frit and become a filtered solution that exits the outlet of the vessel. Devices and methods described herein allow more rapid, cleaner, and inexpensive production of filtered samples than conventional methods.

8 Claims, 4 Drawing Sheets

(51) Int. Cl.
   *G01N 1/34*     (2006.01)
   *G01N 1/38*     (2006.01)
   *G01N 1/40*     (2006.01)
   *G01N 11/08*    (2006.01)
   *G01N 33/543*   (2006.01)

(52) U.S. Cl.
   CPC .......................... *G01N 33/54388* (2021.08); *B01L 2300/0681* (2013.01); *B01L 2300/0825* (2013.01); *E02F 3/907* (2013.01); *G01N 2001/386* (2013.01); *G01N 2001/4088* (2013.01)

(56) References Cited

U.S. PATENT DOCUMENTS

2013/0309700 A1* 11/2013 Hearn ...................... C12Q 1/04
                                                    435/8
2015/0182156 A1*  7/2015 Engbersen ........... G01N 33/491
                                                    435/7.94
2017/0030811 A1   2/2017 Gellibolian et al.
2017/0248500 A1*  8/2017 Holm ................... G01N 33/569

OTHER PUBLICATIONS

International Search Report relating to corresponding application No. PCT/IB2018/054828, completed on Oct. 17, 2018 and dated Oct. 23, 2018.
Examination Report issued in EP Application No. 18755890.3 dated Nov. 2, 2023.

* cited by examiner

DEVICES AND METHODS FOR PREPARING FILTERED SOLUTIONS FOR LATERAL FLOW TESTING

RELATED APPLICATIONS

This application claims the benefit of and priority to U.S. Provisional Patent Application No. 62/529,230 filed on Jul. 6, 2017 titled "DEVICES AND METHODS FOR PREPARING FILTERED SOLUTIONS FOR LATERAL FLOW TESTING," the contents of which are incorporated herein by reference in its entirety.

TECHNICAL FIELD

The present disclosure relates generally to devices and methods for preparing a filtered solution from slurry for lateral flow testing of analytes of interest in agricultural or environmental samples. In particular, the present disclosure relates to devices and methods which employ a porous frit in a vessel to provide rapid, inexpensive, and clean production of filtered samples for use in a lateral flow test.

BACKGROUND

Lateral flow testing is used to assess concentrations of an analyte in solution. In the realm of food safety, lateral flow testing can be used to test for the presence of toxins, such as mycotoxins that can naturally occur on food products destined for animal or human consumption. The robustness of lateral flow testing devices allows for more active testing of products at the source, such as at farms or food-preparation facilities.

SUMMARY

The present disclosure relates to devices and methods for preparation of a filtered solution from slurry for lateral flow testing that employ a porous frit in a vessel wherein positive pressure is applied to the volume enclosed by a vessel body of the vessel.

In one aspect, the present disclosure relates to a method of lateral flow testing using a filtered solution. The method includes mixing a sample with an extraction solution to create a slurry. The method includes placing a porous frit adjacent to an outlet of a vessel. The vessel includes a vessel body enclosing a volume. The method includes placing the slurry into the vessel. The method includes applying a positive pressure to the volume to cause the slurry to pass through the porous frit and become a filtered solution that exits the outlet. The method includes applying the filtered solution to a lateral flow testing device.

In another aspect, the present disclosure relates to devices for preparing a filtered solution from slurry for lateral flow testing of analytes of interest in agricultural or environmental samples. The device includes a vessel including a vessel body enclosing a volume and an outlet. The device also includes a porous frit adjacent to the outlet and means for applying a positive pressure to the volume. Applying a positive pressure to the volume causes a slurry in the vessel body to pass through the porous frit and become a filtered solution that exits the outlet.

Embodiments of the above aspects can include one or more of the following features. In some embodiments, the vessel is a syringe. In some embodiments, the means for applying a positive pressure includes a plunger slideably engaged with the vessel body to allow reduction of the size of the volume. In some embodiments, the means for applying a positive pressure includes a pump attached to an inlet of the vessel, the pump providing positive pressure to the volume. In some embodiments, the filtered solution exits at a rate of at least one drop per second. In some embodiments, a pore size of the porous frit is selected based upon physical properties of a sample included in the slurry.

The devices and methods of the present disclosure provide several advantages over the prior art. For example, the devices and methods of the present disclosure can provide a low cost, rapid, easy to use device for filtering slurry samples for use in lateral flow testing. By passing a slurry through a porous frit, the filtered solution is rapidly obtained that is sufficiently free of particulate to be suitable for lateral flow testing. Devices and methods of the present disclosure can produce filtered samples in less time than conventional devices and methods.

BRIEF DESCRIPTION OF THE DRAWINGS

The invention will be more fully understood from the following detailed description taken in conjunction with the accompanying drawings, in which.

DETAILED DESCRIPTION

Devices and methods described herein provide an economical and rapid way to prepare filtered solutions for lateral flow testing. For example, the devices and methods described herein utilize positive pressure to pass a slurry through a porous frit. The characteristics of the porous frit are chosen based upon physical properties of the sample. By using positive pressure and a porous frit as described herein, filtered sample preparation occurs quickly without sacrificing yield of analytes to be tested in the solution. Devices and methods described herein are particularly adept at processing aerated, frothy, or foamy samples that typically take a lengthy time to filter using conventional gravity-fed methods.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Using conventional devices and methods, a user prepares a slurry from a product to test for the presence of analytes using lateral flow testing. The slurry can be thick and filled with large particulate matter that interferes with proper transit of the sample through a lateral flow testing device. In conventional devices, the slurry is filtered by placing the slurry onto filter paper suspended over a cup and allowing gravity to pull the solution through the filter paper. This procedure including subsequent disposal of the paper filter can be messy and take a significant amount of time to produce a filtered sample of large enough volume to perform lateral flow testing. Devices and methods described herein provide a low-cost, rapid, and clean way to produce filtered samples for lateral flow testing.

Figure 1:
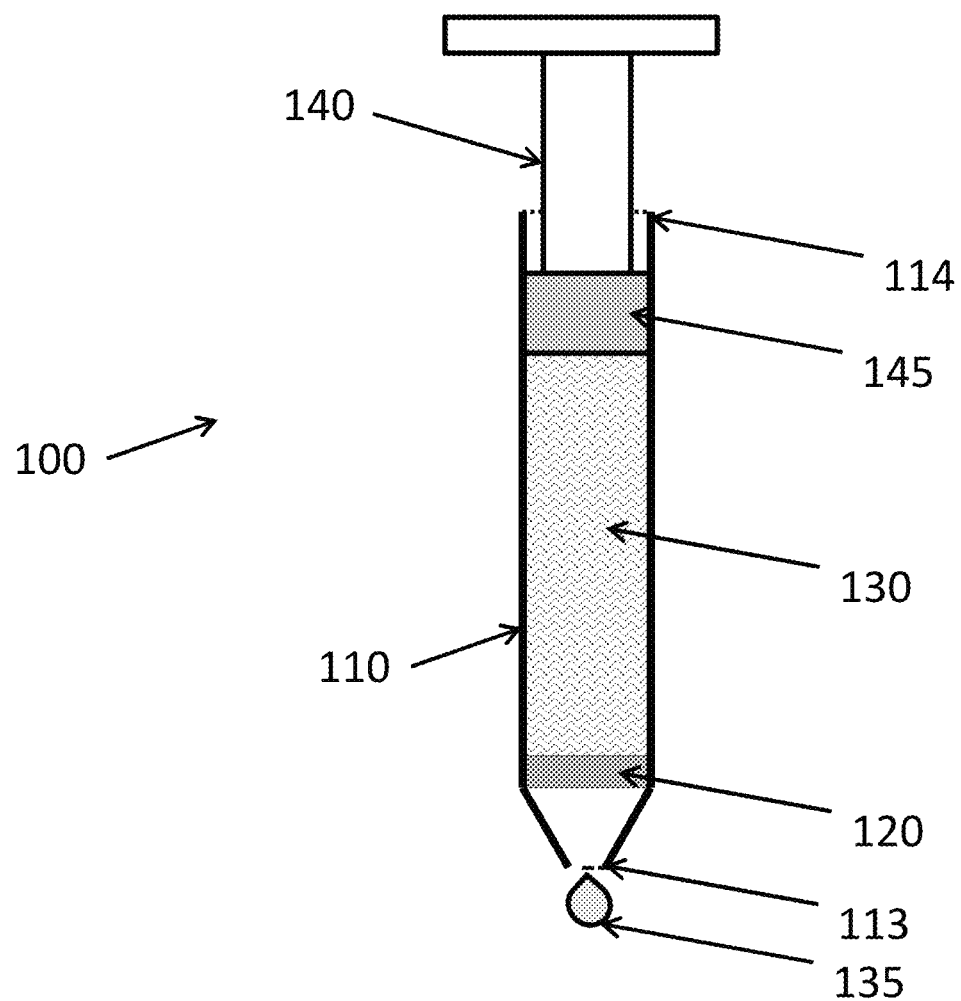
FIG. 1 illustrates a device for preparing a filtered solution from slurry for lateral flow testing in accordance with various embodiments described herein.

FIG. 1 illustrates a device 100 for preparing a filtered solution from slurry for lateral flow testing according to various embodiments described herein. In particular, the device 100 can produce a filtered solution for lateral flow testing of analytes of interest in agricultural or environmental samples. The device 100 includes a vessel 110 including a vessel body 112 enclosing a volume. The vessel 110 has an outlet 113 and an inlet 114. The device 100 also includes a porous frit 120 adjacent to the outlet 113. When a slurry 130 is placed into the volume and positive pressure is applied to the volume, the slurry 130 passes through the porous frit 120 and becomes a filtered solution 135 that exits the outlet 113. The device 100 produces the filtered solution 135 more quickly than conventional devices.

The vessel body 112 can be made of a variety of materials including plastic or glass materials. In some embodiments, the vessel body 112 can include polycarbonate. In some embodiments, the vessel body 112 can include non-reactive materials that are resistant to interaction with materials placed therein. In some embodiments, the volume enclosed in the vessel 110 can be in a range from 200 µL to 15 mL. In a preferred embodiment, the volume of the vessel 110 is 10 mL. In accordance with various embodiments, the vessel 110 can be a syringe. The syringe can be a commercially available syringe or a syringe that is specially manufactured for compatibility with devices and methods described herein. In some embodiments, the vessel 110 can be a column.

Figure 2:
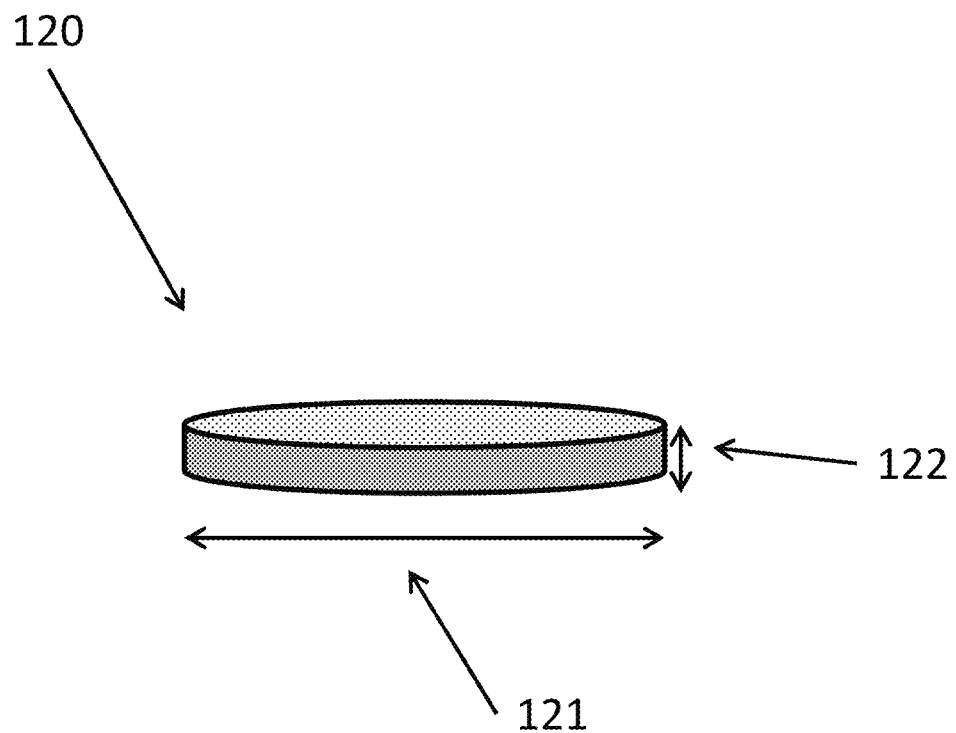
FIG. 2 illustrates a porous frit for use with various devices and methods described herein.

The porous frit 120 can include pores that impede passage of large particles or other debris from the slurry 130 but allow passage of filtered solution including analytes of interest. In some embodiments, the porous frit 120 can include glass fiber, glass fiber wool, glass, polyester, porous plastics such as those from POREX® (Fairburn, GA), or any other appropriate material. The porous frit 120 can be any shape or size that is appropriate to separate the slurry in the volume from the outlet 113 without allowing solution to leak around the frit 120. For example, the porous frit 120 can be cylindrical in embodiments where the vessel 110 has a tubular shape such as in the case of a syringe. As shown in FIG. 2, the porous frit 120 can have a lateral dimension 121 (such as a diameter) and a thickness 122.

The pore size or porosity of the porous frit 120 can be chosen based upon physical properties (e.g., concentration, viscosity, insoluble particle size, or others) of the slurry 130. The slurry 130 is prepared in some embodiments by placing the sample to be tested in an extraction solution to extract the analytes of interest into the slurry. In various embodiments, the sample of interest can include an agricultural product or crop such as corn, peanuts, wheat, or other products. The extraction solution can include water or a specialized solution such as an enzymatic solution. In some embodiments, the extraction solution can include a surfactant. Slurries produced by this process can include different amounts and sizes of fibrous matter or other particulates. For example, certain products may need to be crushed or ground more finely than others. The density and size of particulates in the slurry can affect how quickly the slurry can flow through the porous frit 120. In some embodiments, the pore sizes in the porous frit 120 can be selected in a range from 50 to 700 µm. In some embodiments, a range of pore sizes can be provided in the porous frit 120. Systems and methods described herein can include porous frits having a range of pore sizes such as 90-160 µm or 50-120 µm in a single frit in various embodiments.

In some embodiments, the slurry 130 can be aerated, frothy, or foamy such that small bubbles or air pockets are trapped within the slurry. For example, some extraction solutions used to extract analytes of interest from a sample can include surfactants or other materials that foam upon agitation. Because agitation such as vortexing, mixing, or shaking is a typical step in preparation of the slurry to maximize extraction of analytes, foamy slurries are not uncommon. In some embodiments, the pore size or porosity of the porous frit 120 can be chosen based upon consideration of the level of aeration of the slurry. In conventional systems, foamy slurries pass through filter paper more slowly than non-aerated samples because the back-pressure created by the foam counteracts the gravity-fed filtration system. The application of positive pressure to the slurry 130 in the vessel 110 can overcome the back-pressure to produce a filtered solution at a faster rate than that available with conventional systems.

In some embodiments, the porous frit 120 can be removable or replaceable within the vessel 110. In such embodiments, the porous frit 120 and vessel 110 can be provided or chosen separately and the particular porous frit that is most compatible with the sample to be measured can be selected and installed adjacent the outlet 113 of the vessel 110 by a user. In other embodiments, the porous frit 120 can be installed into the vessel 110 by a manufacturer and may not be removable.

In some embodiments, the slurry 130 can be placed into the vessel body 112 through the inlet 114. In some embodiments, the inlet 114 has a larger diameter than the outlet 113. Means for applying positive pressure to the volume can be applied through the inlet 114 in some embodiments as described below.

The filtered solution 135 can pass out of the outlet 113 and collect in a vial in preparation for lateral flow testing. In some embodiments, the filtered solution 135 can be cloudy or turbid and can include some non-zero amount of particulate material. In some embodiments, the filtered solution 135 can exit the vessel at a rate of at least one drop per second. In some embodiments, the amount of filtered solution 135 needed to perform a lateral flow test can be in a range from 50 µL to 200 µL. In some embodiments, the outlet 113 can be coupled to a cannula or tube to direct or carry the flow of filtered solution 135 from the outlet 113 to the collection vial. In various embodiments, the filtered solution 135 can include analytes related to mycotoxins or metabolic products created therefrom including, but not limited to, aflatoxins, citrinins, deoxynivalenols (vomitoxins), fumonisins, ochratoxins, zearalenones, T-2, and HT-2.

Positive pressure can be applied to the volume enclosed by the vessel body 112 to cause the slurry to pass through the porous frit and exit the outlet 113 as a filtered solution 135. As shown in FIG. 1, positive pressure can be applied in some embodiments using a plunger 140 that enters the vessel body 112 through the inlet 114. The plunger 140 can slideably engage with the vessel body 112 to allow reduction of the size of the volume in some embodiments. The plunger 140 can include a stopper 145 in various embodiments. The stopper 145 can seal against the inside of the vessel body 112. Applying force to the plunger 140 can force the slurry 130 to pass through the porous frit 120 and exit the outlet 113 as filtered solution 135.

Figure 3:
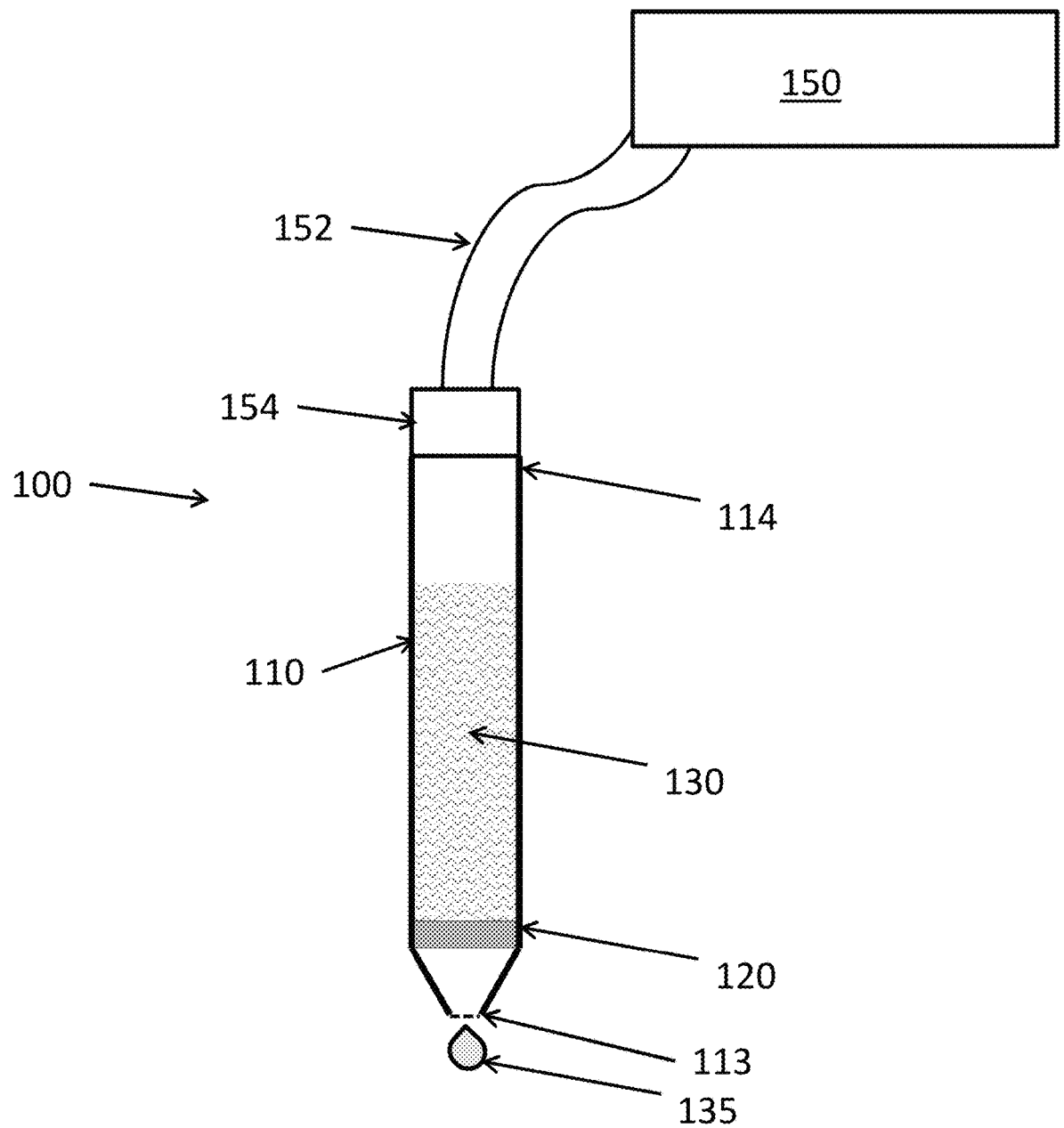
FIG. 3 illustrates a device for preparing a filtered solution from slurry for lateral flow testing in accordance with various embodiments described herein.

As shown in FIG. 3, a mechanical aid may be used to apply positive pressure to the volume in some embodiments.

For example, a pump 150 can be connected to the inlet 114 of the vessel 110 by a hose 152 and a connector 154. In some embodiments, the pump can provide positive pressure to the volume, for example, when power is applied to the pump. In some embodiments, the pressure applied by the pump 150 can be selected based upon the physical properties of the slurry. The pump 150 can provide a pressure in a range from 0 psi to 10 psi. In some embodiments, the pump 150 can be a commodity product such as a commercial aquarium pump. The hose 152 can be made of a range of materials in various embodiments such as polycarbonate, nylon, polyethylene, and others. In some embodiments, the hose 152 is flexible.

The connector 154 can mount to the inlet 114 of the vessel 110 in a variety of ways. In some embodiments, the connector 154 can include screw threads or other securement means that couple to complementary securement means on the vessel body 112 such as screw threads, a lip, or a flange. In some embodiments, the connector 154 can include an o-ring or other sealing means that seals against the inner surface of the vessel body 112 to allow a pressure to build up within the volume without leaks.

In some embodiments, devices and methods described herein can prepare a filtered solution faster than conventional systems and methods. To illustrate some of the advantages of the technology of the present disclosure, the following comparative experiment was conducted.

In this comparative example, performance of a device in accordance with the present disclosure (the "test" system) was compared to the performance of a conventional system. Several agricultural samples were prepared containing a known concentration of contamination associated with mycotoxins such as aflatoxin. The samples were ground, and a slurry was prepared using an extraction solution in accordance with standard procedures. Filtered solutions were prepared using the conventional system and two versions of the test system featuring porous frits with different pore sizes. The time to prepare the filtered solution was measured as well as the final measurement of the concentration of each mycotoxin analyte of interest obtained with a lateral flow test.

In the test, samples included corn contaminated with 4.5+/−0.5 ppb of Aflatoxin B1 (Naturally contaminated corn, Trilogy Analytical Laboratory, Washington, MO) and wheat contaminated with 2.3+/−0.2 ppm of deoxynivalenol (DON), also known as vomitoxin (Naturally contaminated wheat, Trilogy Analytical Laboratory, Washington, MO). The corn samples were processed into a slurry with an AQUA premix solution (VICAM, Milford, MA) while the wheat samples were prepared in deionized water.

To prepare the filtered solution using the conventional system, slurry was placed into a paper filter positioned in a funnel and the slurry was allowed to drain from the paper under gravity to create the filtered solution.

To prepare the filtered solution using the test systems in accordance with the present teachings, the slurry was placed into a blank column (VICAM Myco6in1+, VICAM, Milford, MA) fitted with a porous frit (Interstate Specialty Products, Sutton, MA) with a range of pore sizes of either 90-160 μm or 50-120 μm. The filtered solutions were tested using the appropriate lateral flow testing device for the sample (Afla-V and DON-V strip tests, VICAM, Milford, MA). The results of the test are shown in the table below:

| Analyte | Sample Type | Filter type | Pore Size (μm) | Time to produce 100 μL (mm:ss) | Measured concentration |
|---|---|---|---|---|---|
| Afla-V | Corn | Paper | Coarse | 1:15 | 3.31 ppb |
|  |  | Frit | 90-160 | 0:30 | 3.13 ppb |
| Afla-V | Corn | Paper | Coarse | 1:16 | 3.84 ppb |
|  |  | Frit | 50-120 | 0:24 | 3.28 ppb |
| DON-V | Wheat | Paper | Coarse | 3:39 | 2.12 ppm |
|  |  | Frit | 90-160 | 1:19 | 1.78 ppm |
| DON-V | Wheat | Paper | Coarse | 3:41 | 2.23 ppm |
|  |  | Frit | 50-120 | 1:43 | 1.92 ppm |

The results indicate that filtered samples can be prepared according to devices and methods of the present disclosure significantly faster compared to conventional systems. For example, the time to prepare a filtered solution of sufficient volume for the corn sample can be reduced by ~35%, and the time to prepare a filtered solution of sufficient volume for the wheat sample can be reduced by ~41%).

For some samples (e.g., wheat), the resulting filtered solution can be cloudy or turbid with some quantity of particulate present. Although the presence of some particulate can alter the expected results for such samples, the change in results can be compensated in some embodiments by generating a calibration curve specific to each sample type. For example, the standard curve can be generated using the filtered solution obtained from the test system. That is, the measurement provided by the lateral flow testing device can be adjusted based upon the sample or slurry type and the choice of porous frit 120 in the device 100.

Figure 4:
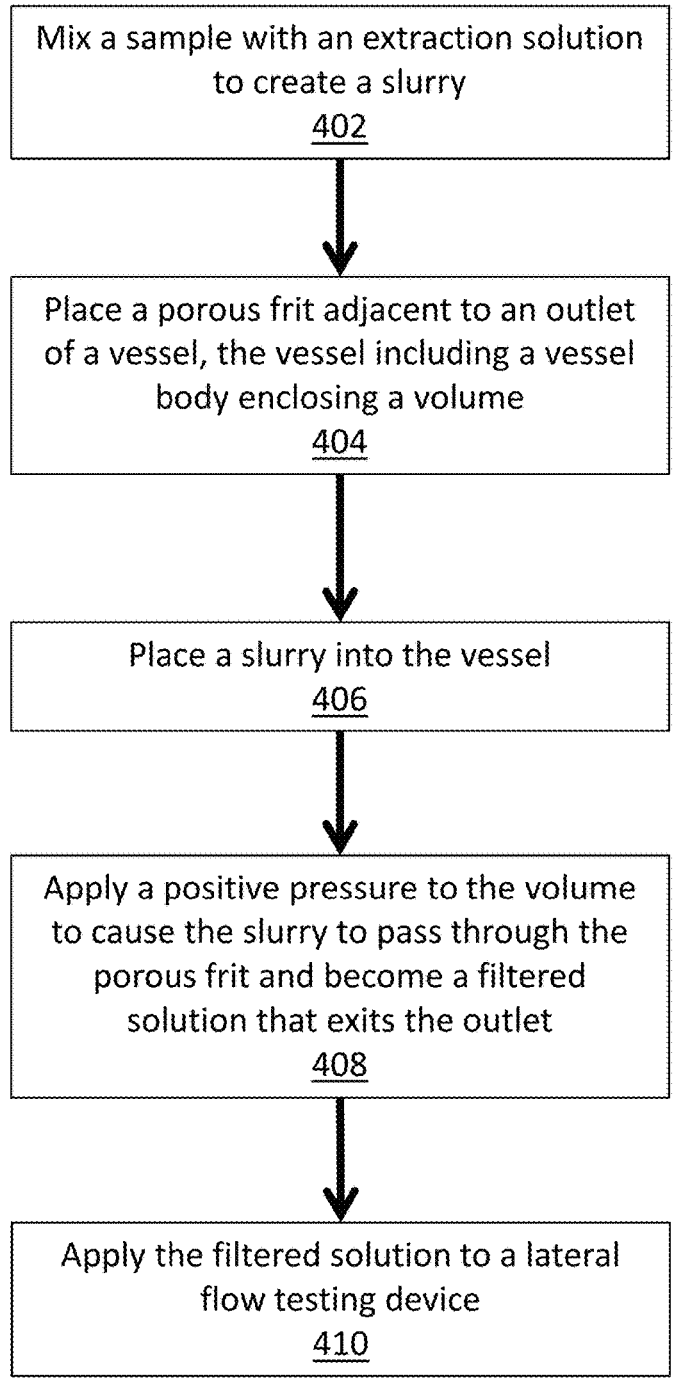
FIG. 4 illustrates a method of lateral flow testing using a filtered solution in accordance with various embodiments described herein.
Figure 4:
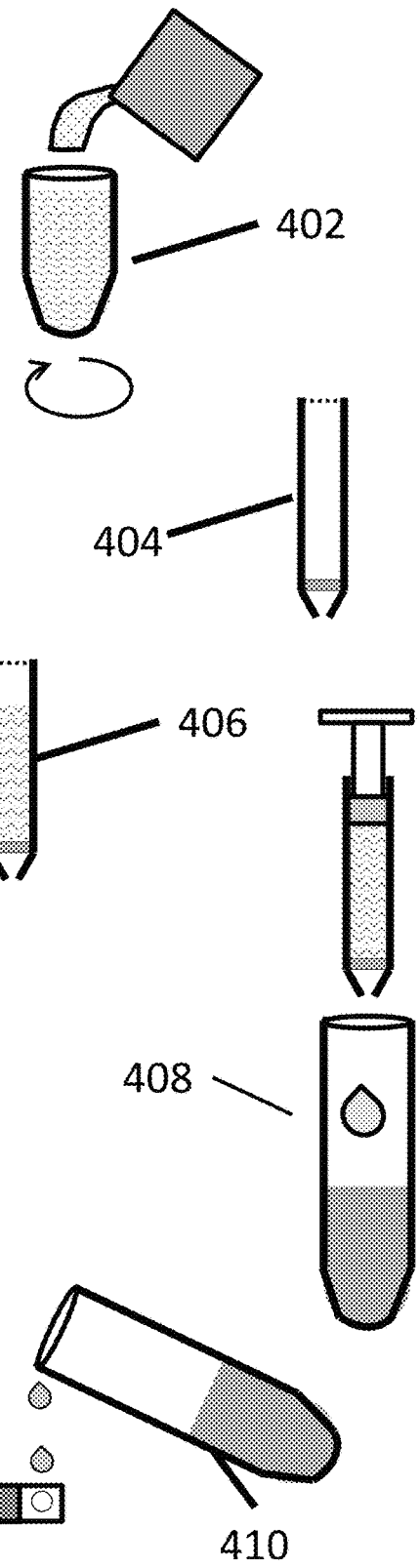

FIG. 4 illustrates a method 400 of lateral flow testing using a filtered solution in accordance with various embodiments described herein. In FIG. 4, each step of the method 400 is illustrated by an accompanying drawing. The method 400 includes mixing a sample with an extraction solution to create a slurry (step 402). As described previously, the sample can be crushed or ground and mixed with the extraction solution under agitation.

The method 400 also includes placing a porous frit adjacent to an outlet of a vessel that includes a vessel body enclosing a volume (step 404). For example, the porous frit 120 can be placed adjacent to the outlet 113 of the vessel 110 including the vessel body 112 as described above with reference to FIGS. 1 and 3. In some embodiments, the porous frit 120 can be chosen to have a certain porosity or pore size based upon consideration of physical properties of the sample. In some implementations, this step is optional as the porous frit may be pre-engaged with the vessel. The method 400 also includes placing a slurry into the vessel (step 406).

The method 400 further includes applying a positive pressure to the volume to cause the slurry to pass through the porous frit and become a filtered solution that exits the outlet (step 408). For example, a plunger 140 or pump 150 can be engaged with the vessel 110 to seal and apply pressure to the volume as described above with reference to FIGS. 1 and 3. In some embodiments, the filtered solution can be collected in a vial.

The method 400 also includes applying the filtered solution to a lateral flow testing device (step 410). For example, the lateral flow testing device can include a lateral flow test cassette having an indicator region and a sample region, and the filtered solution can be applied to the sample region. In various embodiments, the filtered solution can be placed onto the sample region or the sample region can be submerged into a volume of the filtered solution.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component, or step. Likewise, a single element, component, or step may be replaced with a plurality of elements, components, or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other embodiments, functions, and advantages are also within the scope of the invention.

We claim:

1. A method of lateral flow testing using a filtered solution, comprising mixing a sample including analytes related to mycotoxins or metabolic products created therefrom with an extraction solution including a surfactant to create a slurry;

agitating or vortexing the slurry to create a foamy or frothy aerated slurry;

placing a porous frit adjacent to an outlet of a vessel, the vessel including a vessel body enclosing a volume, wherein a pore size of the porous frit is in a range from 50 to 700 micrometers;

placing the aerated slurry into the vessel;

applying a positive pressure to the volume to cause the aerated slurry to pass through the porous frit and become a filtered solution that exits the outlet, wherein the filtered solution includes analytes related to mycotoxins or metabolic products created therefrom; and applying the filtered solution to a lateral flow testing device.

2. The method of claim 1, wherein the step of applying a positive pressure further comprises:

connecting a pump to an inlet of the vessel; and powering the pump.

3. The method of claim 1, wherein the vessel is a syringe.

4. The method of claim 3, wherein the step of applying a positive pressure further comprises:

pressing on a plunger of the syringe, the plunger slideably engaged with the vessel body to allow reduction of the size of the volume.

5. The method of claim 1, wherein the filtered solution exits the outlet at a rate of at least one drop per second.

6. The method of claim 1, wherein the step of placing the porous frit adjacent to the outlet of the vessel further comprises selecting the pore size of the porous frit in the range from 50 to 700 micrometers based upon a level of aeration of the aerated slurry.

7. The method of claim 1, wherein the filtered solution is cloudy.

8. The method of claim 1, wherein the porous frit comprises one or more of porous plastic, glass, or glass fiber wool.

* * * * *